(12) United States Patent
Kim

(10) Patent No.: US 7,451,583 B2
(45) Date of Patent: Nov. 18, 2008

(54) AUTOMATIC MEDICINE PACKAGING MACHINE WITH DOOR LOCK UNIT

(75) Inventor: Jun Ho Kim, Daegu (KR)

(73) Assignee: JVM Co., Ltd., Taegu (KR)

( * ) Notice: Subject to any disclaimer, the term of this patent is extended or adjusted under 35 U.S.C. 154(b) by 0 days.

(21) Appl. No.: 11/754,837

(22) Filed: May 29, 2007

(65) Prior Publication Data

US 2008/0148685 A1    Jun. 26, 2008

(30) Foreign Application Priority Data

Dec. 22, 2006    (KR) .................... 10-2006-0133154

(51) Int. Cl.
*B65B 35/54*    (2006.01)

(52) U.S. Cl. ................ 53/154; 53/168; 53/237; 53/268; 221/83; 221/125; 221/154

(58) Field of Classification Search .............. 53/131.2, 53/52, 154, 168, 237, 268; 221/2, 9, 83, 221/154, 125

See application file for complete search history.

(56) References Cited

U.S. PATENT DOCUMENTS

| | | |
|---|---|---|
| 169,935 A | 11/1875 | Whitman |
| 350,675 A | 10/1886 | Hathaway |
| 488,721 A | 12/1892 | Stempel |
| 1,121,804 A | 12/1914 | Coulson |
| 1,270,756 A | 6/1918 | Holmberg |
| 1,912,248 A | 5/1933 | Bateman et al. |
| 2,005,496 A | 6/1935 | Cleveland |
| 2,181,314 A | 11/1939 | Burns |
| 2,208,951 A | 7/1940 | Tamassy |
| 2,255,036 A | 9/1941 | Gedge |
| 2,449,139 A | 9/1948 | Poanar |
| 2,710,712 A | 6/1955 | Friedman |
| 2,712,883 A | 7/1955 | Esposito et al. |
| 2,918,089 A | 12/1959 | Brown, Jr. et al. |
| 2,994,996 A | 8/1961 | Kiar |
| 3,074,214 A | 1/1963 | Schneider et al. |
| 3,227,127 A | 1/1966 | Gayle |
| 3,263,857 A | 8/1966 | Krakauer et al. |
| 3,348,392 A | 10/1967 | Schrelber |
| 3,408,876 A | 11/1968 | Andrews |

(Continued)

FOREIGN PATENT DOCUMENTS

GB    2178397    2/1987

(Continued)

*Primary Examiner*—Thanh K Truong
(74) *Attorney, Agent, or Firm*—John K. Park; Park Law Firm

(57) ABSTRACT

An automatic medicine packaging machine with door lock unit that prevents the supplement and outflow of tablets by an unauthorized person and makes tablets kept and treated more safely is disclosed. The automatic medicine packaging machine comprising a plurality of tablet cassettes and a door includes; a door lock unit that is established on a body of the automatic medicine packaging machine and locks or unlocks the door; a button operation unit that is established on the front of the body and that operation is inputted by a user; and a lock controller that controls the operation of the door lock unit according to a lock or unlock signal inputted by the button operation unit, in which the lock controller includes a user authentication unit that authenticates user of the door lock unit.

11 Claims, 6 Drawing Sheets

U.S. PATENT DOCUMENTS

| | | |
|---|---|---|
| 3,410,452 A | 11/1968 | Igel et al. |
| 3,481,103 A | 12/1969 | Summerour |
| 3,546,849 A | 12/1970 | Zimmerman |
| 3,562,475 A | 2/1971 | Angelotti et al. |
| 3,604,559 A | 9/1971 | McCall et al. |
| 3,774,368 A | 11/1973 | Paprzycki |
| 3,820,655 A | 6/1974 | La Tourette et al. |
| 3,830,419 A | 8/1974 | Lee |
| 3,842,569 A | 10/1974 | McClelland et al. |
| 3,850,760 A | 11/1974 | Crawford et al. |
| 3,861,651 A | 1/1975 | Takamura |
| 3,871,158 A | 3/1975 | Koenig et al. |
| 3,921,419 A | 11/1975 | Rosenkranz et al. |
| 3,990,209 A | 11/1976 | Eisenberg |
| 4,019,547 A | 4/1977 | Ross |
| 4,149,394 A | 4/1979 | Sornes |
| 4,209,211 A | 6/1980 | Alford |
| 4,244,158 A | 1/1981 | Nelham |
| 4,254,601 A | 3/1981 | Prager et al. |
| 4,267,942 A | 5/1981 | Wick, Jr. et al. |
| 4,382,527 A | 5/1983 | Lerner |
| 4,519,179 A | 5/1985 | Meier |
| 4,534,499 A | 8/1985 | Cox et al. |
| 4,572,376 A | 2/1986 | Wrennall |
| 4,664,289 A | 5/1987 | Shimizu et al. |
| 4,696,392 A | 9/1987 | Chisholm, Jr. |
| 4,771,912 A | 9/1988 | van Wingerden |
| 4,790,118 A | 12/1988 | Chilcoate |
| 4,790,421 A | 12/1988 | Gorges |
| 4,811,764 A * | 3/1989 | McLaughlin .................. 141/98 |
| 4,903,861 A | 2/1990 | Yuyama |
| 4,915,259 A | 4/1990 | Guigan et al. |
| 4,922,682 A | 5/1990 | Tait et al. |
| 4,955,178 A | 9/1990 | Shroyer |
| 5,089,511 A | 2/1992 | Bonin et al. |
| 5,097,652 A | 3/1992 | Inamura et al. |
| 5,219,095 A | 6/1993 | Shimizu et al. |
| 5,221,024 A * | 6/1993 | Campbell ....................... 221/3 |
| 5,318,430 A | 6/1994 | Ramm |
| 5,337,919 A | 8/1994 | Spaulding et al. |
| 5,348,061 A | 9/1994 | Riley et al. |
| 5,381,904 A | 1/1995 | Thurell |
| 5,383,559 A | 1/1995 | Toren |
| 5,413,245 A | 5/1995 | Wright |
| 5,441,165 A * | 8/1995 | Kemp et al. ..................... 221/2 |
| 5,459,983 A | 10/1995 | Sadek et al. |
| 5,481,855 A | 1/1996 | Yuyama |
| 5,487,289 A * | 1/1996 | Otto, III et al. ............. 70/279.1 |
| 5,502,944 A | 4/1996 | Kraft et al. |
| 5,509,573 A | 4/1996 | Campoli |
| 5,522,525 A | 6/1996 | McLaughlin et al. |
| 5,575,465 A | 11/1996 | Auerbach et al. |
| 5,588,792 A | 12/1996 | Tiso |
| 5,599,015 A | 2/1997 | Shimizu et al. |
| 5,611,456 A | 3/1997 | Kasper |
| 5,626,219 A | 5/1997 | Deefholts et al. |
| 5,651,476 A | 7/1997 | Percy et al. |
| 5,652,911 A | 7/1997 | Van Venrooy et al. |
| 5,660,305 A | 8/1997 | Lasher et al. |
| 5,667,096 A | 9/1997 | Wu |
| 5,671,592 A | 9/1997 | Yuyama et al. |
| 5,678,393 A | 10/1997 | Yuyama et al. |
| 5,709,063 A | 1/1998 | Yuyama et al. |
| 5,722,215 A | 3/1998 | Yuyama |
| 5,749,117 A | 5/1998 | Forsline |
| 5,765,606 A | 6/1998 | Takemasa et al. |
| 5,787,678 A | 8/1998 | Koike et al. |
| 5,797,248 A | 8/1998 | Hetherington et al. |
| 5,803,309 A | 9/1998 | Yuyama et al |
| 5,819,500 A | 10/1998 | Haraguchi et al. |
| 5,839,257 A | 11/1998 | Soderstrom et al. |
| 5,865,342 A | 2/1999 | Ito et al. |
| 5,875,610 A | 3/1999 | Yuyama et al. |
| 5,901,876 A | 5/1999 | Yuyama et al. |
| 5,927,546 A | 7/1999 | Yuyama et al. |
| 5,930,145 A | 7/1999 | Yuyama et al. |
| 5,944,057 A | 8/1999 | Pierce |
| 5,946,883 A | 9/1999 | Yuyama et al. |
| 5,963,453 A | 10/1999 | East |
| 5,964,374 A | 10/1999 | Yuyama et al. |
| 5,987,859 A | 11/1999 | Dreger |
| 6,012,602 A | 1/2000 | Yuyama et al. |
| 6,023,916 A | 2/2000 | Bouthiette |
| 6,029,683 A | 2/2000 | Moebs et al. |
| 6,050,064 A | 4/2000 | Yuyama et al. |
| 6,089,136 A | 7/2000 | Hinojosa et al. |
| 6,109,486 A | 8/2000 | Lee, Jr. et al. |
| 6,119,440 A | 9/2000 | Benner, Jr. et al. |
| 6,119,892 A | 9/2000 | Laurent et al. |
| 6,145,700 A | 11/2000 | Takahashi et al. |
| 6,164,038 A | 12/2000 | Kim |
| 6,170,229 B1 | 1/2001 | Kim |
| 6,170,230 B1 | 1/2001 | Chudy et al. |
| 6,170,699 B1 | 1/2001 | Kim |
| 6,179,205 B1 | 1/2001 | Sloan |
| 6,202,385 B1 | 3/2001 | Kim |
| 6,216,418 B1 | 4/2001 | Kim |
| 6,256,963 B1 | 7/2001 | Kim |
| 6,263,639 B1 | 7/2001 | Kim |
| 6,273,335 B1 | 8/2001 | Sloan |
| 6,308,494 B1 | 10/2001 | Yuyama et al. |
| 6,311,743 B1 | 11/2001 | Baroncini |
| 6,318,051 B1 | 11/2001 | Preiss |
| 6,349,848 B1 | 2/2002 | Uema et al. |
| 6,364,517 B1 | 4/2002 | Yuyama et al. |
| 6,367,232 B2 | 4/2002 | Kim |
| 6,394,308 B1 | 5/2002 | Yuyama et al. |
| 6,409,290 B1 | 6/2002 | Lin |
| 6,427,865 B1 | 8/2002 | Stillwell et al. |
| 6,449,921 B1 | 9/2002 | Kim |
| 6,457,611 B1 | 10/2002 | Koehler |
| 6,471,089 B2 | 10/2002 | Liff et al. |
| 6,471,090 B1 | 10/2002 | Inamura et al. |
| 6,478,186 B1 | 11/2002 | Willach et al. |
| 6,481,180 B1 | 11/2002 | Takahashi et al. |
| 6,508,279 B2 | 1/2003 | Siegel et al. |
| 6,540,101 B1 | 4/2003 | Kim |
| 6,581,356 B2 | 6/2003 | Kim |
| 6,585,132 B2 | 7/2003 | Kim |
| 6,604,019 B2 | 8/2003 | Ahlin, deceased et al. |
| 6,611,733 B1 | 8/2003 | De La Huerga |
| 6,644,504 B2 | 11/2003 | Yuyama et al. |
| 6,647,702 B1 | 11/2003 | Kim |
| 6,722,167 B1 | 4/2004 | Hsu |
| 6,772,907 B2 | 8/2004 | Kim |
| 6,786,356 B2 | 9/2004 | Geiger et al. |
| 6,792,736 B1 | 9/2004 | Takahashi et al. |
| 6,805,259 B2 | 10/2004 | Stevens et al. |
| 6,898,919 B2 | 5/2005 | Kim |
| 7,028,447 B2 | 4/2006 | Sung |
| 7,059,098 B2 | 6/2006 | Kim |
| 7,331,151 B2 | 2/2008 | Kim |
| 2002/0092275 A1 | 7/2002 | Kim |
| 2003/0057225 A1 | 3/2003 | Kim |
| 2003/0074868 A1 | 4/2003 | Yasuoka et al. |
| 2004/0046020 A1 | 3/2004 | Andreasson et al. |
| 2004/0129716 A1* | 7/2004 | Naufel et al. .................. 221/9 |
| 2004/0182044 A1 | 9/2004 | Kim |
| 2005/0179349 A1* | 8/2005 | Booth et al. ............. 312/257.1 |
| 2005/0234430 A1* | 10/2005 | Mao et al. ................. 604/890.1 |
| 2006/0058918 A1* | 3/2006 | Handfield et al. ........... 700/236 |
| 2006/0070352 A1 | 4/2006 | Morich |
| 2006/0139148 A1* | 6/2006 | Faro et al. .................... 340/5.73 |
| 2006/0267727 A1* | 11/2006 | Cayne et al. ................ 340/5.22 |

| | | |
|---|---|---|
| 2006/0273106 A1 | 12/2006 | Kim |
| 2007/0016327 A1 | 1/2007 | Yuyame et al. |
| 2007/0078562 A1* | 4/2007 | Park, IV .................. 700/243 |
| 2007/0125100 A1* | 6/2007 | Shoenfeld ................. 62/125 |
| 2007/0151204 A1 | 7/2007 | Kim |
| 2007/0208595 A1 | 9/2007 | Ohmura et al. |

| | | | |
|---|---|---|---|
| 2007/0257773 A1* | 11/2007 | Hill et al. ................. | 340/5.73 |

FOREIGN PATENT DOCUMENTS

| | | |
|---|---|---|
| JP | 9-175510 | 7/1997 |
| JP | 9-266940 | 10/1997 |

* cited by examiner

FIG. 5 [PRIOR ART]
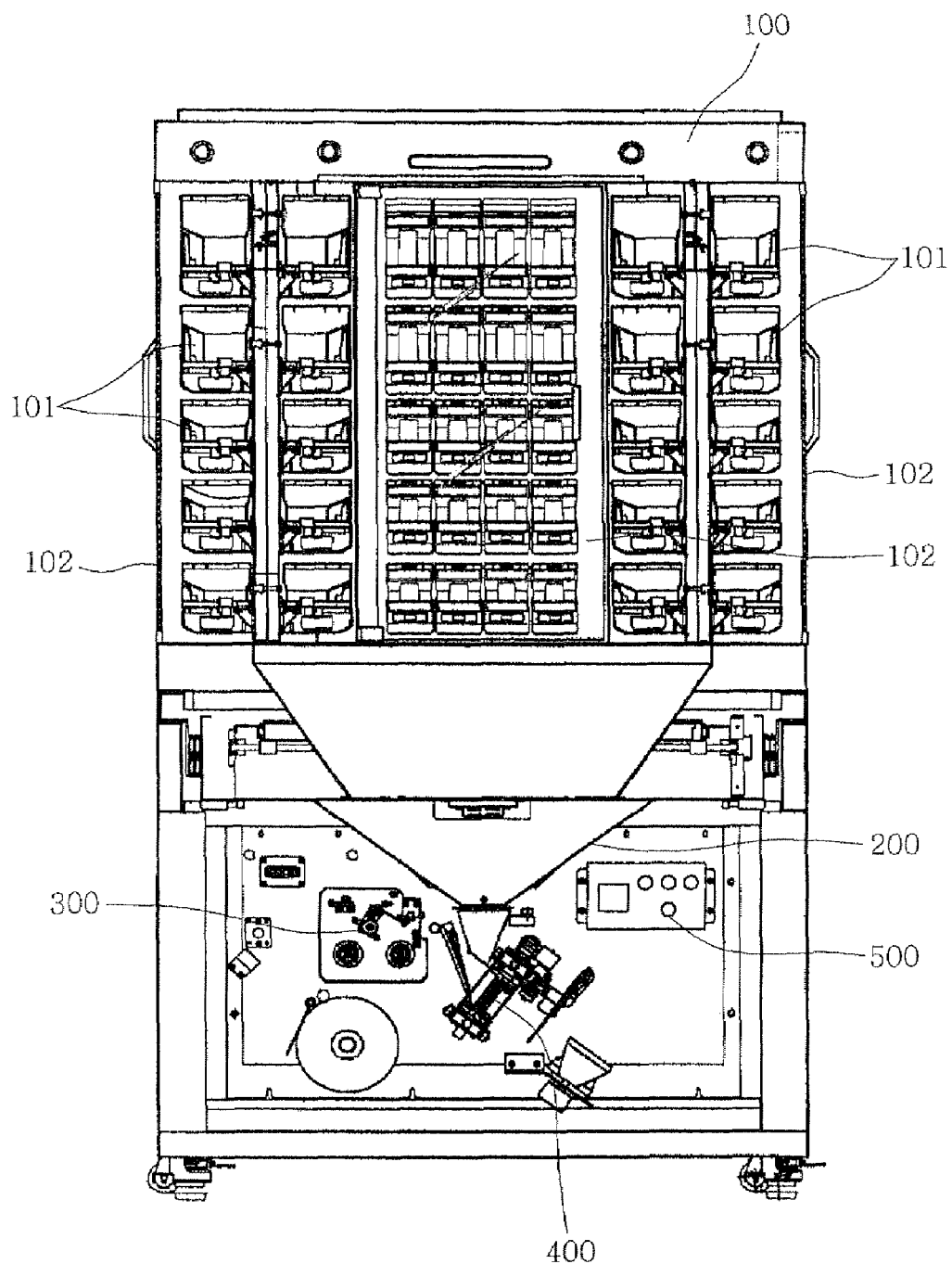

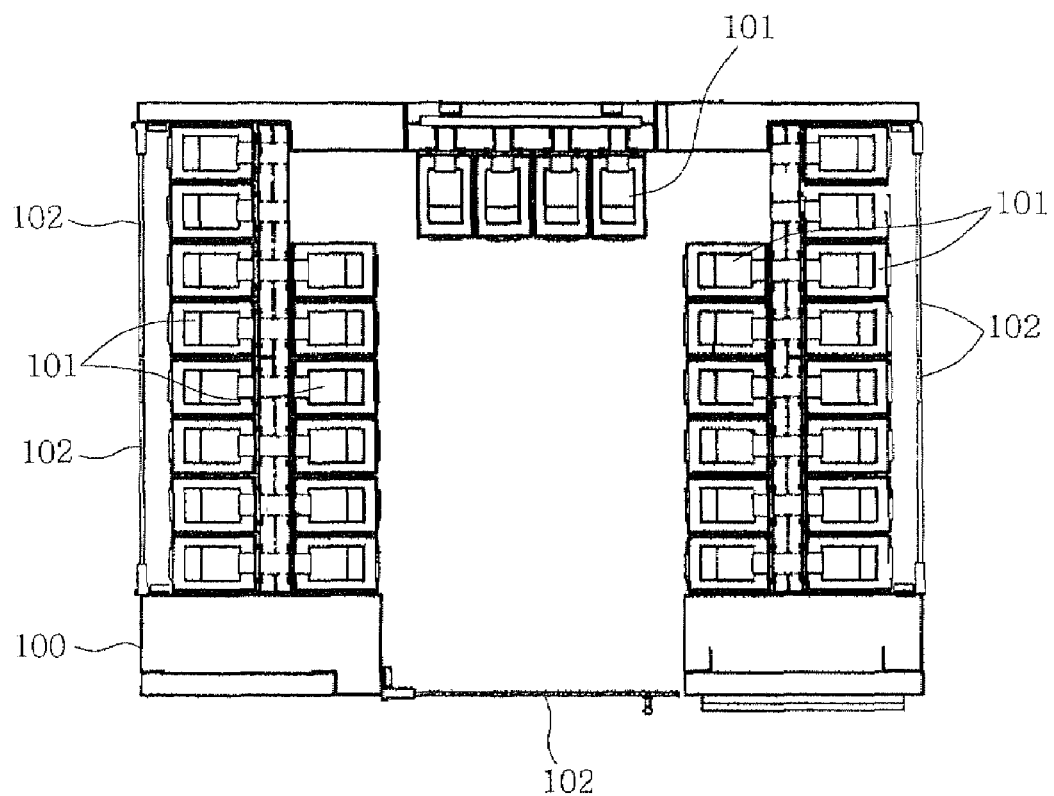
FIG. 6 [PRIOR ART]

AUTOMATIC MEDICINE PACKAGING MACHINE WITH DOOR LOCK UNIT

CLAIMING FOREIGN PRIORITY

The applicant claims and requests a foreign priority, through the Paris Convention for the Protection of Industrial Property, based on patent applications filed in the Republic of Korea (South Korea) with the filing date of Dec. 22, 2006 with the patent application number 10-2006-0133154 by the applicant, the contents of which are incorporated by reference into this disclosure as if fully set forth herein.

BACKGROUND OF THE INVENTION

The present invention relates to an automatic medicine packaging machine that packages each dose of medication. Specifically, the present invention relates to the automatic medicine packaging machine with door lock unit that prevents the supplement and outflow of tablets by an unauthorized person and makes tablets kept and treated more safely.

In general, an automatic medicine packaging machine continuously packages tablet-type medications that are dispensed per dose. The construction and operation of the same inventor's Korea patent 'Tablet automatic dispensing and packaging apparatus' with Korea patent number 10-0611949 filed on Aug. 7, 2006 is explained as follows using FIG. 5 and FIG. 6.

Referring to FIG. 5, the automatic medicine packaging machine includes a body 100, in which a plurality of tablet cassettes 101 is arrayed in the interior of the body 100 and a door 102 for opening and closing the interior of the body 100, a hopper 200 constructed below the interior of the body 100 that traps tablets which have been dispensed from the tablet cassettes 101, a printing unit 300 that prints instructions to each package of tablets dispensed by the hopper 200, a sealing unit 400 that feeds and seals tablets in the hopper 200 by tablet envelope(s) on which instruction labels are printed by the printing unit 300, and a controller 500 which controls the tablet cassettes 101, the printing unit 300, and the sealing unit 400. The controller 500 operates to export tablets per dose from the tablet cassettes 101 to the hopper 200, and tablets exported to the hopper 200 will be fallen to and filled in medication envelope(s). Tablets per dose exported to tablet envelope(s) form a tablet package by heat-sealing process of the sealing unit 400.

Referring to FIG. 6, the tablet cassettes 101 are arrayed in the interior of the body 100 and the door 102 is established in the front and sides of the body 100, so that the interior of the body 100 is possible to be open or close by the door 102. Because the interior of the body 100 is possible to be open or close, tablets may be supplemented to or outflowed from the tablet cassettes 101 by a user.

However, the above prior art has a disadvantage that the supplement or outflow of tablets may be easily done by an unauthorized person, so that tablets which have been dispensed into tablet cassettes may not be preserved safely and also the supplement of tablets may not be made exactly.

SUMMARY OF THE INVENTION

The present invention contrives to solve the above disadvantage of the prior art and improves the same inventor's Korea patent 'Tablet automatic dispensing and packaging apparatus' with Korea patent number 10-0611949 filed on Aug. 7, 2006.

An objective of the invention is to provide an automatic medicine packaging machine with door lock unit that prevents the supplement and outflow of tablets by an unauthorized person and makes tablets kept and treated more safely.

Another objective of the invention is to provide an automatic medicine packaging machine with door lock unit in which the door can be opened or closed by manual operation in case of power failure and the convenience of usage may be improved due to manual operation.

Still another objective of the invention is to provide an automatic medicine packaging machine with door lock unit in which, by detecting open or close state of the door, locking of the door can be done more precisely and the state may be recognized by a user with ease.

Still another objective of the invention is to provide an automatic medicine packaging machine with door lock unit in which abnormal opening of the door will be prohibited and abnormal opening may be recognized by a user smoothly.

In order to accomplish the above objectives of the invention based on a preferred embodiment, an automatic medicine packaging machine comprising a plurality of tablet cassettes arrayed in the interior of a body and a door for opening and closing the body and continuously packaging each dose of medication by extracting tablets from the tablet cassettes includes: a door lock unit that is established on the body of the automatic medicine packaging machine and locks or unlocks the door; a button operation unit that is established on the front of the body and receives operation command inputted by a user; and a lock controller that controls the operation of the door lock unit according to a lock or unlock signal inputted by the button operation unit, in which the lock controller includes a user authentication unit that authenticates user of the door lock unit.

The door is established in each of the front and both sides of the interior of the body.

The door lock unit includes a driver that is controlled by the lock controller and an anchor member that locks or unlocks the door by being vertically moved by the driver.

The door lock unit further includes a groove member that is established on the upper part of the door corresponding to the lower part of the anchor member and makes the anchor member to be inserted into or pulled out of the groove member.

The door lock unit further includes a manual operation unit that locks or unlocks the door lock unit by manual operation of a user during power failure.

The manual operation unit includes an on/off switch that is established on the body as a state of being connected to the driver, a battery that is connected to the on/off switch and provides power to the driver, and a key operation unit that is exposed outside the body and controls the driver's operation of locking or unlocking by turning on/off power to be supplied to the driver.

In the door lock unit, the user authentication is done by authentication information inputted by the button operation unit.

In the door lock unit, the user authentication is done by a biometric identifier that is established on the front of the body and on a side of the button operation unit.

In the door lock unit, the user authentication is done by a card reader that is established on the front of the body and inputs user's card information.

The automatic medicine packaging machine further includes an open/close detection sensor that is established on the body corresponding to the door and inputs into the lock controller by detecting a state of the door's being locked or unlocked.

The automatic medicine packaging machine further includes a display that is established on the front of the body and displays the door's opening or closing state inputted from the lock controller.

The automatic medicine packaging machine further includes a beep generation unit that is connected to the lock controller and makes beep sound for warning in case of abnormal opening of the door.

The automatic medicine packaging machine further includes a user's resumé storage unit that is connected to the lock controller and stores users' resumés which are authenticated by the user authentication unit.

The automatic medicine packaging machine further includes a printer that is connected to the lock controller and prints users' resumés stored in the user's resumé storage unit according to a user's operation through the button operation unit.

The present invention has an advantageous effect that prevents the supplement and outflow of tablets by an unauthorized person and makes tablets kept and treated more safely.

The present invention has another advantageous effect that the open-close door can be opened or closed by manual operation in the case of power failure and the convenience of usage may be improved due to manual operation.

The present invention has another advantageous effect that by detecting the open or close state of the door the locking of door can be done more precisely and the state may be recognized by a user with ease.

The present invention has another advantageous effect that the abnormal opening of the door will be prohibited and the abnormal opening may be recognized by a user smoothly.

BRIEF DESCRIPTION OF THE DRAWINGS

These and other features, aspects and advantages of the present invention will become better understood with reference to the accompanying drawings, wherein:

FIG. 5 is an elevation view of an automatic medicine packaging machine by prior art.

FIG. 6 is a plan view of the automatic medicine packaging machine by prior art.

DETAILED DESCRIPTION OF THE PREFERRED EMBODIMENT

Figure 1:
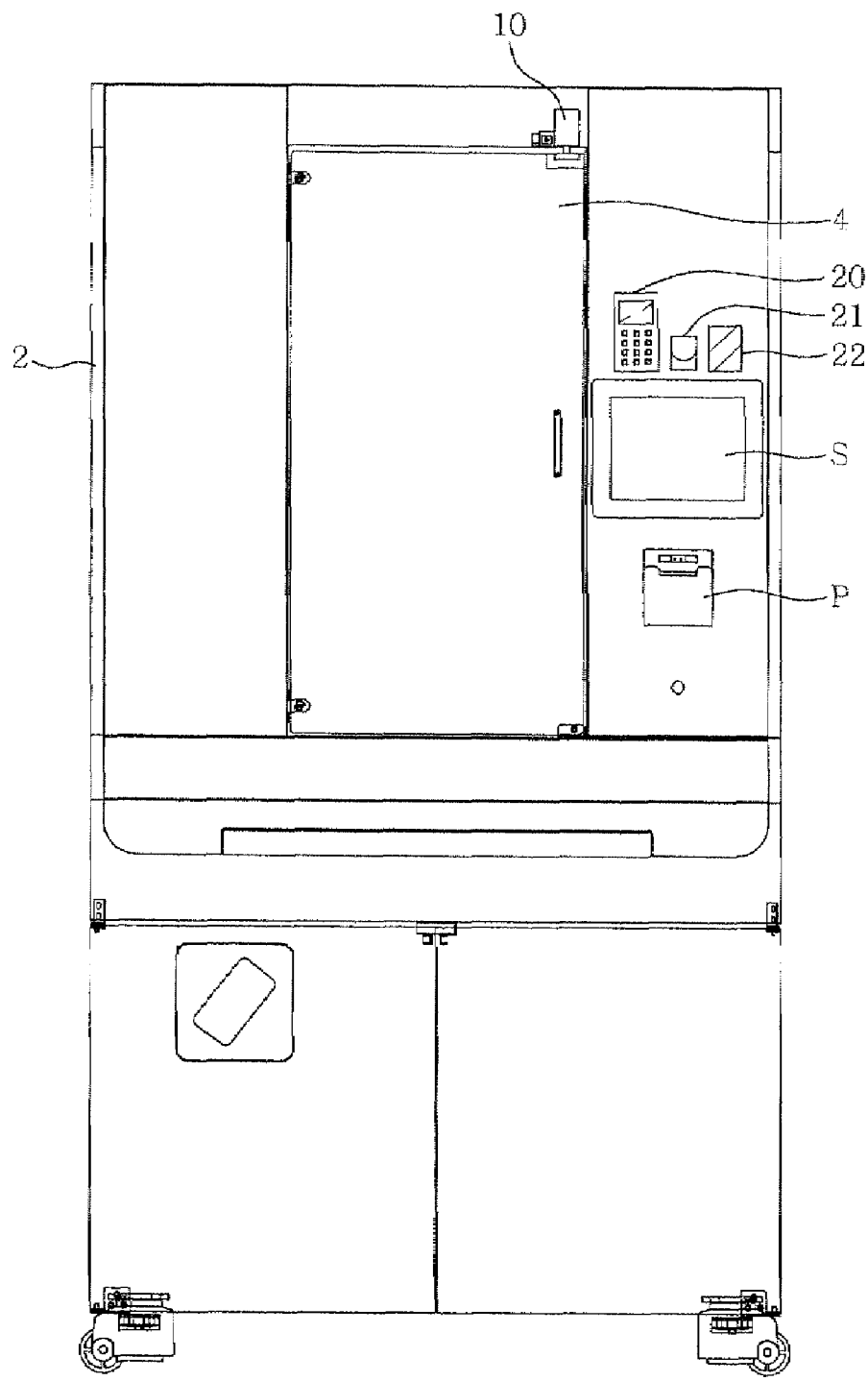
FIG. 1 is an elevation view of an automatic medicine packaging machine with door lock unit according to the present invention.
Figure 2:
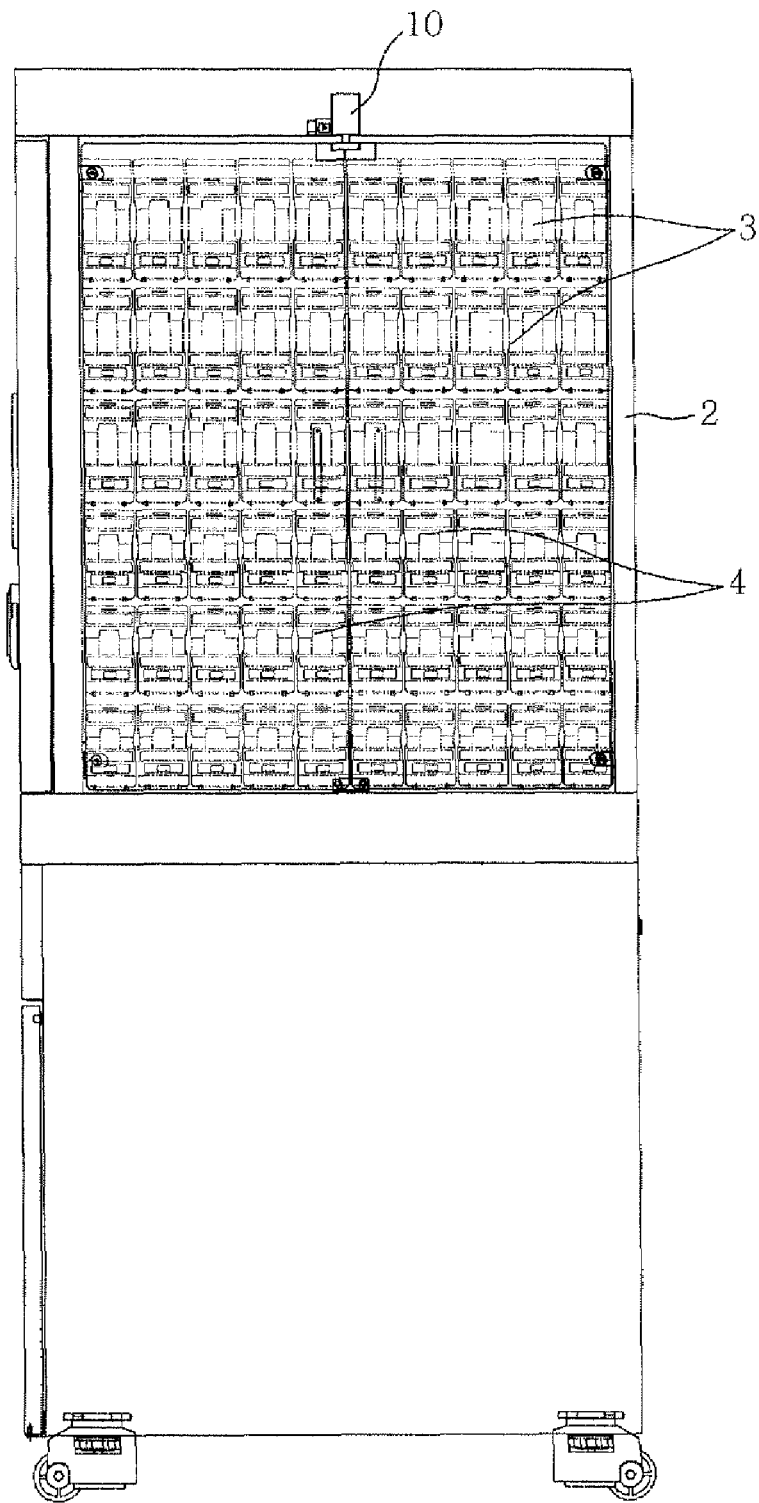
FIG. 2 is a side elevation view of the automatic medicine packaging machine with door lock unit.

Referring to FIG. 1 and FIG. 2, an automatic medicine packaging machine includes a plurality of tablet cassettes 3 arrayed in the interior of a body 2 and a door 4 established in each of the front and sides of the interior of the body 2 for opening and closing the body 2 and continuously packages each dose of medication by extracting tablets from the tablet cassettes 3.

The automatic medicine packaging machine includes a door lock unit 10 that is established in the front and sides of the body 2 of the automatic medicine packaging machine corresponding to the upper part of the door 4 and a button operation unit 20 that is established on the front of the body 2.

The door lock unit 10 automatically locks or unlocks the upper part of the door 4 by operation of a user.

The button operation unit 20 plays a role of inputting authentication information to authenticate a user of the door lock unit 10 by operation of a user and simultaneously inputs a locking or unlocking signal to lock or unlock the door 4 by the door lock unit 10.

The user authentication of the door lock unit 10 is done by authentication information, that is, personal identification numbers or passwords, inputted by the button operation unit 20, but various arts may be applied for authentication.

The user authentication of the door lock unit 10 is also done by a biometric identifier 21 that is established on the front of the body 2 and on a side of the button operation unit 20. The biometric identifier 21 is for smooth user authentication when a user forgot authentication information, in addition to the user authentication through the input of authentication information.

The biometric identifier 21 that plays the above-identified role may independently authenticate a user without being inputted by the button operation unit 20, which is an art of common knowledge for authenticating a user by recognizing human being like a fingerprint identifier which identifies a fingerprint of human being, an iris identifier which identifies an iris of human being, or a voice identifier which identifies a voice of human being.

The user authentication of the door lock unit 10 is also done by a card reader 22 that is established on the front of the body 2. The art of the card reader 22 is an art of common knowledge for authenticating a user by recognizing and reading Integrated Circuit (IC) card information inputted by a user.

The user authentication by the card reader 22 may be independently used without getting authentication information inputted by the button operation unit 20 or may be subsidiarily used in case of being forgotten authentication information, that is, personal identification numbers or passwords, which will be inputted to the button operation unit 20.

In the FIG. 1 there are a touch screen S which is a display apparatus and a label printer P which prints labels.

Figure 3:
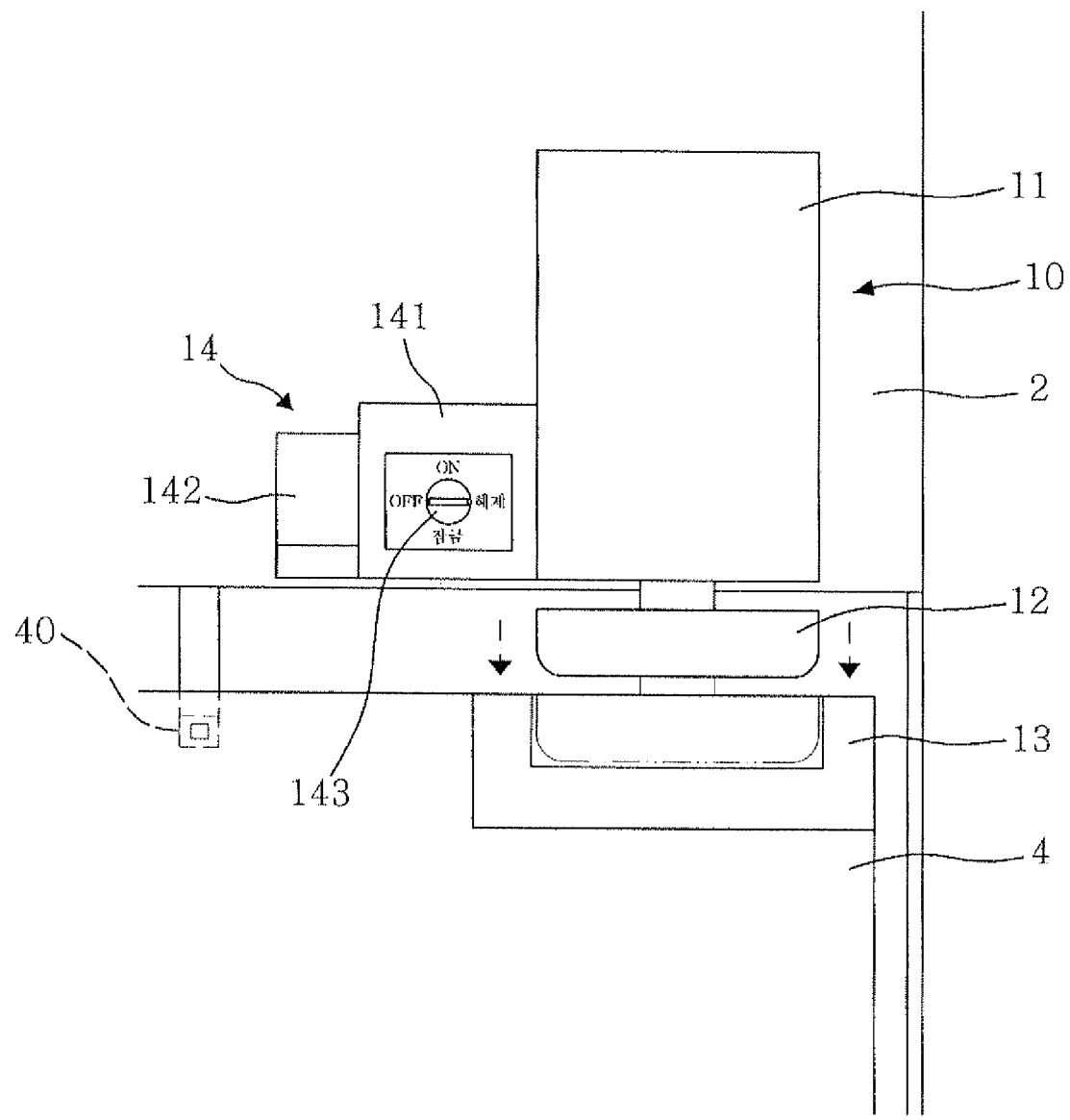
FIG. 3 is an enlarged partial elevation view of the automatic medicine packaging machine with door lock unit.
Figure 4:
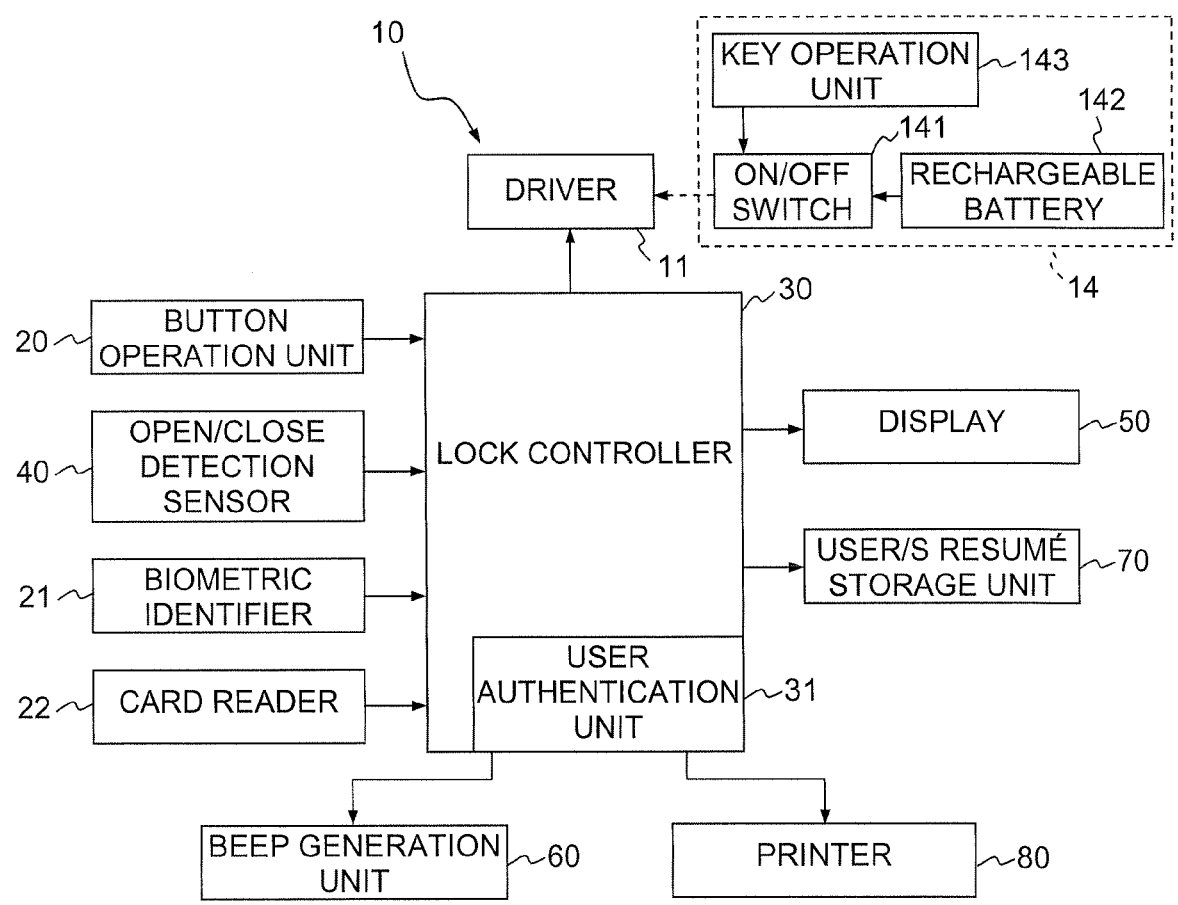
FIG. 4 is a block diagram for the automatic medicine packaging machine with door lock unit.

Referring to FIG. 3 and FIG. 4, the automatic medicine packaging machine includes the door lock unit 10 that locks or unlocks the door 4, the button operation unit 20 that operates the door lock unit 10, the lock controller 30 that controls the operation of the door lock unit 10.

The door lock unit 10 that is established in the body 2 and releasably locks the door 4 includes a driver 11 that is established in the body 2 corresponding to the upper part of the door 4 and controlled by the lock controller 30, an anchor member 12 that locks or unlocks the door 4 by being moved vertically by the driver 11, and a groove member 13 that is established on the upper part of the door 4 corresponding to the lower part of the anchor member 12.

If a user inputs a locking signal into the lock controller 30, then the lock controller 30 operates the driver 11 to insert the anchor member 12 into the groove member 13, and hence the door 4, on which the groove member is attached on the upper part, can be solidly fixed by the anchor member 12.

Conversely, if a user inputs an unlocking signal into the lock controller 30, then the lock controller 30 operates the driver 11 to pull the anchor member 12 out of the groove member 13, and hence unlocking of the door 4 can be accomplished by the anchor member 12.

The driver 11 can be embodied through a motor or a solenoid because the driver 11 can be operated to make the anchor member 12 vertically moved.

The door lock unit 10 further includes a manual operation unit 14 that locks or unlocks the door lock unit 10 by manual operation of a user during power failure.

The manual operation unit 14 allows manual operation of locking or unlocking of the door lock unit 10 by a user with a key in case of unexpected power failure in the automatic medicine packaging machine.

The manual operation unit 14 includes an on/off switch 141 that is established on the body 2 as a state of being connected to the driver 14, a battery 142 that is connected to the on/off switch 141 and provides power to the driver 14, and a key operation unit 143 that is exposed outside the body 2 and controls the driver's 11 operation of locking or unlocking by turning on/off power to be supplied to the driver 11.

When locking or unlocking of the door lock unit 10 may not be performed through the button operation unit 20 in case of power failure, following alternative steps may be sequentially proceeded: a user inserts and rotates a key into the key operation unit 143, power changes from off to on by the on/off switch 141, the door lock unit 10 operates to be unlocked in a state of power on, the door lock unit 10 changes from the operation of unlocking to locking, and finally the door lock unit 10 changes from the operation of locking to power off.

In other words, if a user operates the on/off switch 141 through the key operation unit 143 by inserting a key into the key operation unit 143, then the on/off switch 141 makes power on/off in between the rechargeable battery 142 and the driver 142 according to the rotating position of the key, or locking or unlocking of the door 4 may be manually performed by controlling operation of the driver 11.

The button operation unit 20 that is established on the front of the body 2 plays a role of outputting to the lock controller 30 by being inputted operation of a user, and a user inputs user authentication information through the button operation unit 20 and simultaneously inputs a locking or unlocking signal of the door lock unit 10 into the lock controller 30.

If authentication information is inputted into the lock controller 30 by the button operation unit 20, then an user authentication unit 31 authenticates a user by comparing and analyzing inputted authentication information and authentication information stored in advance.

As another tool of user authentication in addition to the button operation unit 20, a biometric identifier 21 does user authentication alternatively or in case of being forgotten authentication information. The biometric identifier 21 inputs biometric information like a fingerprint, an iris or a voice of a user into the lock controller 30, and user authentication will be performed by the user authentication unit's 31 comparing and analyzing inputted biometric information and biometric information stored in advance.

As still another tool of user authentication in addition to the button operation unit 20, a card reader 22 does user authentication alternatively or in case of being forgotten authentication information. The card reader 22 reads Integrated Circuit (IC) card information of a user, inputs into the lock controller 30, and then user authentication will be performed by the user authentication unit's 31 comparing and analyzing inputted card information and card information stored in advance.

The lock controller 30 includes the user authentication unit 31 which authenticates a user of the door lock unit 10 and controls operation of the door lock unit 10 according to a signal of locking or unlocking inputted by the button operation unit 20.

In other words, the lock controller 30 authenticates a user by confirming authentication information inputted by the button operation unit 20 through user authentication unit 31 and simultaneously locks or unlocks the door 4 by controlling the driver 11 of the door lock unit 10 according to a locking or unlocking signal inputted through the button operation unit 20.

The automatic medicine packaging machine further includes an open/close detection sensor 40 that is established on the body 2 corresponding to the door 4 and inputs into the lock controller 30 by detecting a state of the door's 4 being locked or unlocked.

The open/close detection sensor 40 is a kind of contact sensor which recognizes a state of being open or close of the door 4 through contact or separation of the door 4 established in the body 2 and the open/close detection sensor 40 enables more precise locking because operation of the door lock unit 10 is done in a state of the door's 4 complete closing.

The automatic medicine packaging machine further includes a display 50 that is established on the front of the body 2 and displays the door's 4 opening or closing state inputted from the lock controller 30.

The display 50 is controlled by the lock controller 30 and makes locking or unlocking operation of the door 4 performed more precisely and conveniently by letting a user smoothly recognize a state of locking or unlocking of the door 4 by displaying information detected by the open/close detection sensor 40, that is, a state of locking or unlocking of the door 4.

The display 50 may be independently established on the front of the body 2 or a touch screen which is already established on the front of the body 2 may play the same role.

The automatic medicine packaging machine further includes a beep generation unit 60 that is connected to the lock controller 30 and makes beep sound for warning in case of abnormal opening of the door 4.

The beep generation unit 60 generates a beep by operation of the lock controller 30 if separation of the door 4 is detected by the open/close detection sensor 40 when the door 4 is separated by an unauthorized user while the door 4 is locked after a locking signal's being inputted by a user.

In other words, the lock controller 30 judges a state of the door's 4 being abnormally opened by an authorized person according to present state and information of the open/close detection sensor 40, and the lock controller 30 operates the beep operation unit 60 to make a beep outside.

The automatic medicine packaging machine further includes a user's resumé storage unit 70 that is connected to the lock controller 30 and stores users' resumés which are authenticated by the user authentication unit 31 of the lock controller 30.

The user's resumé storage unit 70 forms resumés on the door lock unit's 10 users by sequentially storing information on users who are authenticated by the user authenticated unit 31 while being controlled by the lock controller 30.

The users' resumés that are stored in the user's resumé storage unit 70 will be displayed on the display 50 according to operation of a user through the button operation unit 20 and makes a user conveniently confirm users of the door lock unit 10.

The automatic medicine packaging machine further includes a printer 80 that is connected to the lock controller 30 and prints users' resumés stored in the user's resumé storage unit 70 according to a user's operation through the button operation unit 20.

The printer 80 may be independently established on the front of the body 2 or a label printer which is already established on the front of the body 2 may play the same role.

While the invention has been shown and described with reference to different embodiments thereof, it will be appreciated by those skilled in the art that variations in form, detail, compositions and operation may be made without departing from the spirit and scope of the invention as defined by the accompanying claims.

What is claimed is:

1. An automatic medicine packaging machine comprising a plurality of tablet cassettes arrayed in the interior of a body and a door for opening and closing the body and continuously packaging each dose of medication by extracting tablets from the tablet cassettes, the automatic medicine packaging machine comprises:
   a) a door lock unit that is established in the body of the automatic medicine packaging machine and locks or unlocks the door;
   b) a button operation unit that is established on the front of the body and receives operation command inputted by a user;
   c) a lock controller that controls the operation of the door lock unit according to a locking or unlocking signal inputted by the button operation unit;
   d) a hopper that is adapted to trap tablets which have been dispensed from the tablet cassettes;
   e) a printing unit that is adapted to print instructions to each package of tablets dispensed by the hopper; and
   f) a sealing unit that is adapted to feed and seal tablets in the hopper by tablet envelope(s) on which instruction labels are printed by the printing unit;
   wherein the lock controller comprises a user authentication unit that authenticates user of the door lock unit;
   wherein the door lock unit comprises a driver that is controlled by the lock controller and an anchor member that locks or unlocks the door by being vertically moved by the driver;
   wherein the door lock unit further comprises a manual operation unit that locks or unlocks the door lock unit by manual operation of a user; and
   wherein the manual operation unit further comprises an on/off switch that is established on the body as a state of being connected to the driver, a battery that is connected to the on/off switch and provides power to the driver, and a key operation unit that is exposed outside the body and controls the driver's operation of locking or unlocking by turning on/off power to be supplied to the driver.

2. The automatic medicine packaging machine of claim 1, wherein the door is established in each of the front and both sides of the interior of the body.

3. The automatic medicine packaging machine of claim 1, wherein the door lock unit further comprises a groove member that is established on the upper part of the door corresponding to the lower part of the anchor member and makes the anchor member to be inserted into or pulled out of the groove member.

4. The automatic medicine packaging machine of ciaim 1, wherein the user authentication of the door lock unit is done by authentication information inputted by the button operation unit.

5. The automatic medicine packaging machine of claim 1, wherein the user authentication of the door lock unit is done by a biometric identifier that is established on the front of the body and on a side of the button operation unit.

6. The automatic medicine packaging machine of claim 1, wherein the user authentication of the door lock unit is done by a card reader that is established on the front of the body and inputs user's card information.

7. The automatic medicine packaging machine of claim 1, further comprising an open/close detection sensor that is established on the body corresponding to the door and inputs into the lock controller by detecting a state of the door's being locked or unlocked.

8. The automatic medicine packaging machine of claim 7, further comprising a display that is established on the front of the body and displays the door's opening or closing state inputted from the lock controller.

9. The automatic medicine packaging machine of claim 7, further comprising a beep generation unit that is connected to the lock controller and makes beep sound for warning in case of abnormal opening of the door.

10. The automatic medicine packaging machine of claim 1, further comprising a user's resumé storage unit that is connected to the lock controller and stores users' resumés which are authenticated by the user authentication unit.

11. The automatic medicine packaging machine of claim 10, further comprising a printer that is connected to the lock controller and prints users' resumés stored in the user's resumé storage unit according to a user's operation through the button operation unit.

* * * * *